United States Patent [19]
Archibald

[11] 4,303,073
[45] Dec. 1, 1981

[54] ELECTROSURGERY SAFETY MONITOR

[75] Inventor: G. Kent Archibald, White Bear Lake, Minn.

[73] Assignee: Medical Plastics, Inc., Milford, Conn.

[21] Appl. No.: 113,106

[22] Filed: Jan. 17, 1980

[51] Int. Cl.³ .............................................. A61B 17/36
[52] U.S. Cl. ................................ 128/303.13; 128/798; 128/908
[58] Field of Search ...................... 128/303.13, 303.14, 128/303.17, 734, 783, 798, 802, 803, 908

[56] References Cited

U.S. PATENT DOCUMENTS

| | | | |
|---|---|---|---|
| 3,601,126 | 8/1971 | Estes | 128/303.14 |
| 3,605,728 | 9/1971 | Ogle | 128/908 |
| 3,642,008 | 2/1972 | Bolduc | 128/798 |
| 3,699,389 | 10/1972 | Holsinger | 128/908 |
| 3,699,968 | 10/1972 | Bolduc | 128/303.18 |
| 3,812,858 | 5/1974 | Oringer | 128/303.14 |
| 3,848,600 | 11/1974 | Patrick | 128/303.13 |
| 3,889,184 | 6/1975 | Bass | 128/908 |
| 3,895,635 | 7/1975 | Justus | 128/303.13 |
| 3,897,787 | 8/1975 | Ikuno | 128/303.14 |
| 3,905,373 | 9/1975 | Gonser | 128/303.14 |
| 3,913,583 | 10/1975 | Bross | 128/303.14 |
| 3,923,063 | 12/1975 | Andrews | 128/303.14 |
| 3,929,137 | 12/1975 | Gonser | 128/303.14 |
| 3,960,141 | 6/1976 | Bolduc | 128/303.13 |
| 4,051,855 | 10/1977 | Schneiderman | 128/303.14 |
| 4,068,699 | 1/1978 | Niemi | 128/908 |
| 4,088,133 | 5/1978 | Twentier | 128/303.13 |
| 4,092,985 | 6/1978 | Kaufman | 128/303.13 |
| 4,094,320 | 6/1978 | Newton | 128/303.14 |
| 4,102,341 | 7/1978 | Ikuno | 128/303.14 |
| 4,102,347 | 7/1978 | Yukl | 128/421 |
| 4,102,348 | 7/1978 | Hihara | 128/422 |
| 4,109,223 | 8/1978 | Tenkman | 128/303.13 |
| 4,114,623 | 9/1978 | Meinke | 128/303.14 |
| 4,117,846 | 10/1978 | Williams | 128/303.13 |
| 4,122,854 | 10/1978 | Blackett | 128/303.13 |
| 4,123,673 | 10/1978 | Gonser | 128/303.14 |
| 4,166,465 | 9/1979 | Esty et al. | 128/303.13 |
| 4,200,104 | 4/1980 | Harris | 128/303.14 |

FOREIGN PATENT DOCUMENTS

| | | |
|---|---|---|
| 2814061 | 10/1978 | Fed. Rep. of Germany ................... 128/303.13 |
| 2414812 | 9/1979 | France ............................. 128/303.13 |

*Primary Examiner*—Lee S. Cohen
*Attorney, Agent, or Firm*—Kinney, Lange, Braddock, Westman and Fairbairn

[57] ABSTRACT

An electrosurgery safety monitor senses a parameter indicative of the area of contact between the return electrode of an electrosurgery system and the body of the patient. An alarm is provided if the area of contact between the return electrode and the body is less than a predetermined amount.

40 Claims, 7 Drawing Figures

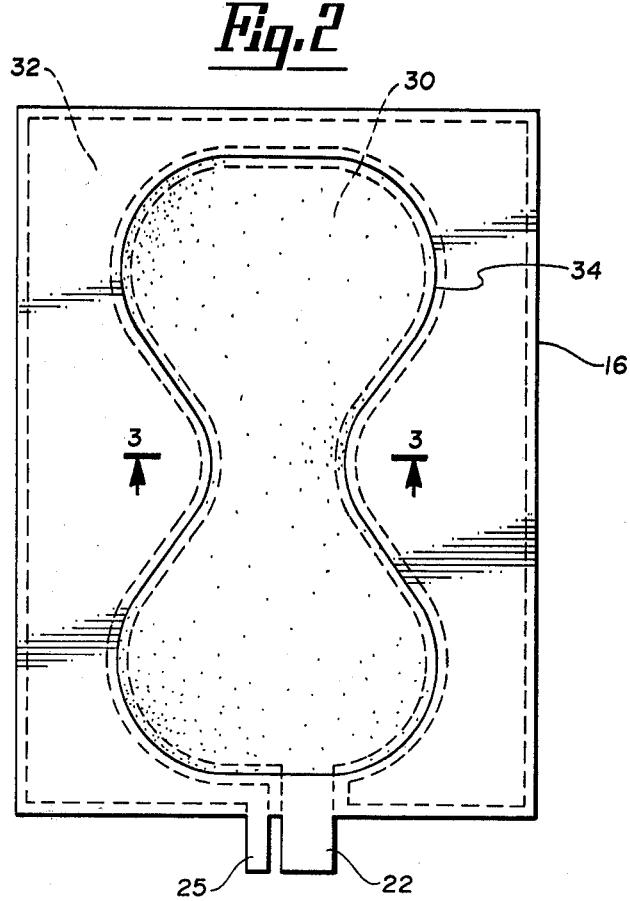
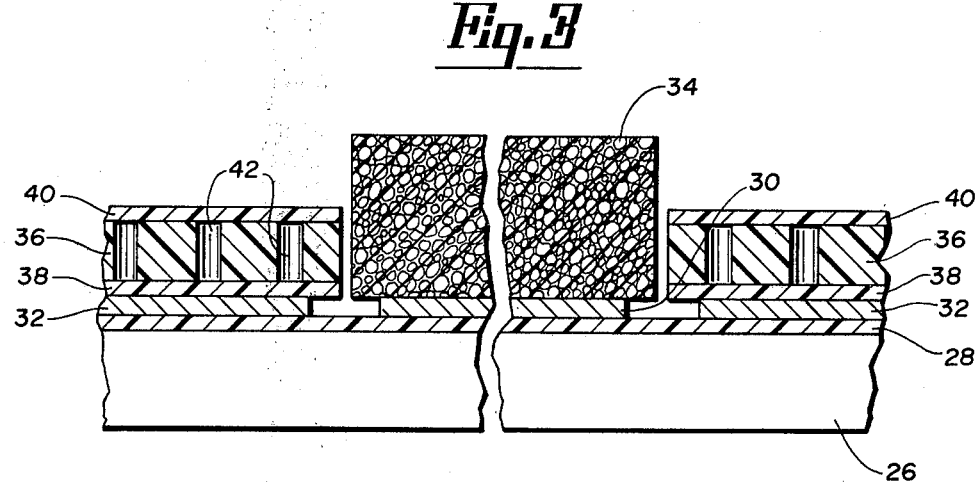
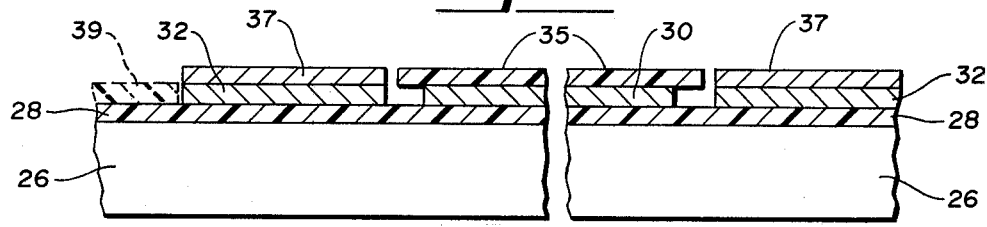

ELECTROSURGERY SAFETY MONITOR

BACKGROUND OF THE INVENTION

1. Field of the Invention

This invention relates to electrosurgery apparatus. In particular, the present invention relates to a safety device which monitors the area of contact between the patient and the return electrode.

2. Description of the Prior Art

Although electrosurgery apparatus has been known for many years, it has grown in importance and has achieved wide use in recent years. A typical electrosurgery apparatus includes a current generator which supplies a high frequency electric current to an active electrode. This active electrode is normally a pencil shaped instrument which is held by the surgeon. A return electrode (which is sometimes called a "dispersive electrode" or "patient plate") is connected to the current generator with a return electrical conductor and makes electrical contact with the patient. In operation, therefore, the high frequency electric current flows from the current generator through the active electrode, through the patient's body to the return electrode, where it is returned to the current generator through the return electrical conductor.

Because of the small contact area at the active electrode—body interface, a high current density exists which causes a surgical effect. In contrast, the return electrode is large in size in comparison to the active electrode, and therefore the current density at this interface is low enough that no surgical effect occurs.

If a portion of the return electrode is not in contact with the patient, the effective area of the return electrode is reduced, thereby resulting in increased current density at the return electrode—patient interface. This increased current density may result in injury to the patient.

In the prior art, this hazard potential has been dealt with in a number of ways. The most common approach is to monitor the current going to the active electrode and the current from the return electrode and compare the magnitude of the two. If the active current is greater than the return current by a given amount, an alarm signal is produced. This approach assumes that if the active conductor current is greater than the return conductor current by a given amount, the return current is taking some alternate path which may be hazardous to the patient. Examples of other systems which sense return current are shown in the following U.S. Pat. Nos.: Estes 3,601,126; Ikuno et al 3,897,787; Bross 3,913,583; Newton et al 4,094,320; Ikuno et al 4,102,341; and Meinke et al 4,114,623.

The basic problem with this approach is that the criteria for alarm of the monitoring system does not relate directly to the area of contact of the return electrode to the patient. For example, a return electrode with only a small area of contact to the patient may conduct all of the return current, and therefore no alarm signal would be produced even though the current density may be high enough to burn the patient. Another problem with this approach is that the current must go through alternate paths to establish an alarm condition, therefore the patient is subjected to a hazardous condition at the time of alarm. Still another problem with this approach is that because of leakage currents (e.g. capacitive coupling of active and return electrode leads and of patient to ground), the disparity between the active and return currents required to signal an alarm must be larger than a safe amount.

Another prior art approach, as described by Blackett in U.S. Pat. No. 4,122,854, is to monitor the potential of the return electrical conductor at the generator with respect to a ground reference. If the return path is open, current will return through alternate paths causing the potential of the return electrical conductor to increase with respect to ground reference. This apparatus has the same deficiencies as described above. First, the monitoring system is not sensitive to the effective return electrode contact area. Second, at the time of an alarm condition the patient is subjected to a hazardous condition. Another patent showing a similar approach is Gonser U.S. Pat. No. 3,905,373.

Still another prior art approach, as described by Bolduc in U.S. Pat. No. 3,642,008, is to section the return electrode and monitor the continuity between sections. The theory behind this approach is that if the return electrode is in contact with the patient, the patient's body will provide the connection between sections. An alarm condition exists if no contact is made between sections. This approach, however, does not relate to the area of contact between return electrode and patient, in that only a portion of each section need be in contact with the patient to satisfy the monitor. Also, the conductive gel that is normally used to interface the return electrode to the patient can provide conductive connections between sections without the return electrode being in contact with the patient.

Still another prior art approach limits the amount of current to which the return electrode-to-patient interface can be subjected. As with all prior art monitor methods, however, the integrity of return electrode to patient contact is not monitored.

Other U.S. Pat. Nos. showing electrosurgery apparatus include Oringer 3,812,858; Andrews et al 3,923,063; Gonser 3,929,137; Schneiderman 4,051,855; Tankman et al 4,109,223; Gonser 4,123,673; and Holsinger 3,699,389.

Examples of return electrodes are shown in the following U.S. Pat. Nos.: Bolduc 3,699,968; Patrick, Jr. et al 3,848,600; Justus et al, 3,895,635; Bolduc 3,960,141; Twentier 4,088,133; Kaufman 4,092,985; Williams 4,117,846; and Esty et al 4,166,465.

The following U.S. Pat. Nos. relate to safety devices for medical electronic devices or equipment, but are not concerned with electrosurgery: Ogle 3,605,728; Bass 3,889,184; Niemi 4,068,699; Yulk 4,102,347; and Hihara et al 4,102,348.

SUMMARY OF THE INVENTION

The present invention is an electrosurgery safety monitor which senses a parameter indicative of the area of contact between the return electrode of an electrosurgery system and the body of the patient. If the area of contact between the return electrode and the body is less than a predetermined amount, an alarm signal is provided.

The safety monitor of the present invention preferably senses capacitance between the body and an electrically conductive layer which is electrically isolated from the body, but which forms a part of the return electrode. The capacitance at the return electrode-body interface is a function of the area of the return electrode which is contacting the patient. This capacitance is monitored, and if the value is not within a specified range, an alarm signal is produced.

BRIEF DESCRIPTION OF THE DRAWINGS

FIG. 2 is a top view of a preferred embodiment of a return electrode for use in conjunction with the safety monitor of the present invention.

FIG. 3 is a partial sectional view along section 3—3 of FIG. 2.

FIG. 3A is a partial sectional view of another embodiment of a return electrode for use in conjunction with the safety monitor of the present invention.

DETAILED DESCRIPTION OF THE PREFERRED EMBODIMENTS

Figure 1:
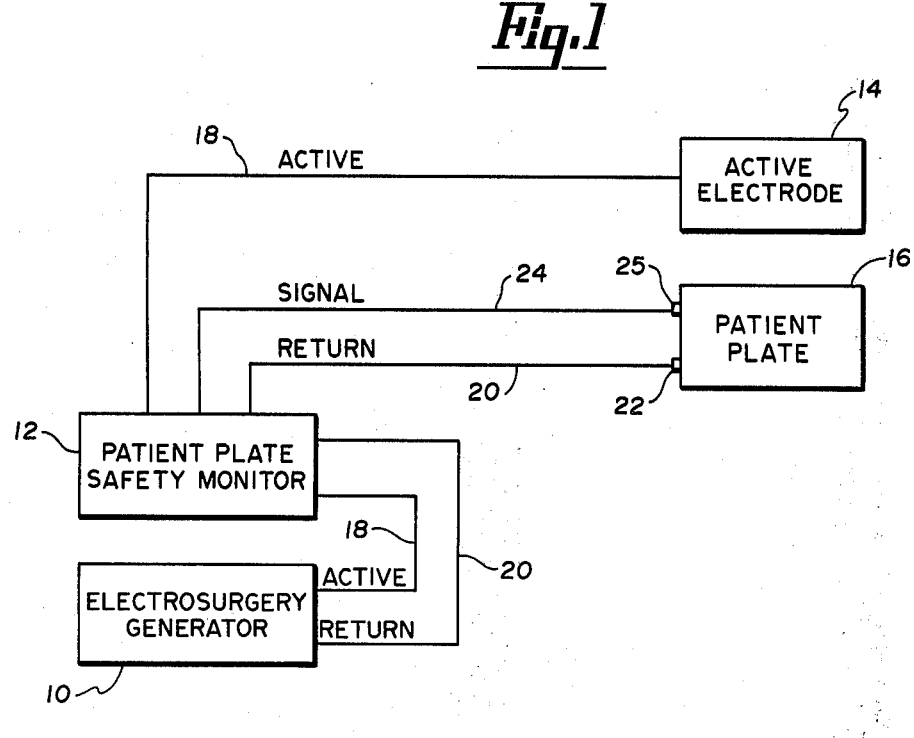
FIG. 1 is an electrical block diagram view of an electrosurgery system utilizing the safety monitor of the present invention.

In FIG. 1, a block diagram of an electrosurgery system using the safety monitor of the present invention is shown. The electrosurgery system includes electrosurgery generator 10, safety monitor 12, active electrode 14, and return electrode 16. As illustrated in FIG. 1, active line 18 is supplied from electrosurgery generator 10, through safety monitor 12, and to active electrode 14. Similarly, return line 20 is connected from electrosurgery generator 10, through safety monitor 12, to terminal 22 of return electrode 16. In addition, a signal line 24 is connected from safety monitor 12 to terminal 25 of return electrode 16.

Safety monitor 12 and return electrode 16 of the present invention may be used in conjunction with conventional electrosurgery generators 10 and active electrodes 14. Although shown in separate blocks in FIG. 1, it should be recognized that the safety monitor 12 of the present invention may be physically housed in the same housing as an electrosurgery generator.

In the present invention, the area of contact between the return electrode 16 and the body of the patient is monitored. If the area of contact between the return electrode 16 and the body is less than a predetermined amount, an alarm signal is provided by safety monitor 12.

In the preferred embodiments of the present invention, safety monitor 12 senses capacitance between the body and an electrically conductive layer of return electrode 16 which is electrically insulated from the body, but which forms a part of return electrode 16. This capacitance is monitored by safety monitor 12 by means of a signal line 24 and return line 20. The capacitance of the return electrode—body interface is a function of the area of return electrode 16 which is in contact with the patient's body. By monitoring the capacitance, safety monitor 12 is sensing a parameter which is a function of the area of contact between return electrode 16 and the patient's body.

In a preferred embodiment of the present invention, safety monitor 12 provides a charging current on signal line 24 to return electrode 16. This charging current charges the return electrode-to-patient capacitance for a predetermined time period. Safety monitor 12 then monitors the voltage between signal line 24 and return line 20, since this voltage is a function of the return electrode-to-patient capacitance. As long as the voltage between lines 20 and 24 remains within a predetermined range, the amount of contact between the return electrode 16 and the body is sufficient so that the dangerous condition does not exist. If, however, the voltage between signal and return lines 24 and 20 falls outside of the predetermined range, safety monitor 12 provides an indication to the medical personnel that a potentially unsafe condition exists.

FIGS. 2 and 3 show a preferred embodiment of return electrode 16 of the present invention. FIG. 2 is a top view of return electrode 16, while FIG. 3 is a sectional view of a portion of return electrode 16 along section 3—3 of FIG. 2.

As shown in FIGS. 2 and 3, return electrode 16 includes substrate 26, which is preferably a foam or other material having sufficient structural strength to support the remainder of the return electrode structure, while being sufficiently flexible to conform to the body of the patient.

Overlying substrate 26 is first bonding layer 28, which is preferably a 0.5 mil thick polyester sheet having adhesive on both sides. The adhesive on the bottom surface of first bonding layer 28 is attached to substrate 26.

Overlying and attached to first bonding layer 28 are electrodes 30 and 32. Electrode 30 is attached to terminal 22 and has a generally "figure eight" shape. Electrode 32 is connected to terminal 25 and surrounds electrode 30. In a preferred embodiment of the present invention, both electrode 30 and electrode 32 are formed by aluminum foil laminate having a thickness of between about 4 and about 6 mils. The aluminum foil is attached to the adhesive on the upper surface of bonding layer 28.

Attached and electrically connected to electrode 30 is contact pad 34. As shown in FIGS. 2 and 3, contact pad 34 has a shape which is generally the same as electrode 30. Pad 34 is in electrical contact with electrode 30, but is electrically isolated from electrode 32. In one preferred embodiment, pad 34 is an open cell pad of fibrous material which is impregnated with a conductive gel. It is contact pad 34 which makes ohmic contact with the body of the patient.

In other preferred embodiments of the present invention, pad 34 is replaced by a conductive material such as a conductive gel or conductive adhesive. In other embodiments, contact with the patient is made directly by electrode 30, and pad 34 is eliminated.

Overlying electrode 32 is a dielectric layer 36, which is bonded to electrode 32 by second bonding layer 38. On the top surface of dielectric layer 36 is a third bonding layer 40. In a preferred embodiment, bonding layers 38 and 40 are 0.5 mil polyester sheets having adhesive on both sides. When return electrode 16 is in use, the adhesive on the top surface of third bonding layer 40 is attached to the body of the patient causing the entire return electrode 16 to be held in position on the patient's body.

In a preferred embodiment of the present invention, dielectric layer 36 is a vinyl sheet having a thickness of about 8-20 mils and having a plurality of holes 42 extending through the vinyl sheet. Holes 42 preferably comprise about 25-75 percent of the area of dielectric layer 36. By properly selecting the thickness and material forming dielectric layer 36, together with the percentage of area consumed by holes 42, it is possible to select the proper effective dielectric constant for the capacitor which will be formed between electrode 32 and the body of the patient.

As shown in FIGS. 2 and 3, a capacitance exists between electrodes 30 and 32. When return electrode 16 is attached to the body of a patient, electrode 30 makes ohmic contact with the patient through gel impregnated pad 34 (or other conductive means, as discussed above). The capacitance between electrode 32 and the patient's body (and thus between electrode 32 and electrode 30) is a function of the amount of area of third bonding layer 40 which is in contact with the patient's body. The smaller the area of contact between third bonding layer 40 and the patient's body, the higher the capacitance.

In the present invention, the capacitance between electrodes 30 and 32 is monitored and, when the capacitance falls outside of predetermined range, an alarm signal is produced. Although the capacitance is a measure of the contact between third bonding layer 40 and the body, with the illustrated configuration of electrodes 30 and 32 and pad 34, it is unlikely that all or nearly all of third bonding layer 40 could be in contact with the patient's body without pad 34 being in contact with the patient's body. This is because pad 34 extends above the top surface of bonding layer 40, and bonding layer 40 completely surrounds pad 34.

Although FIGS. 2 and 3 show a preferred configuration of the return electrode 16 of the present invention, other configurations are also possible. In particular, return electrode 16 may be configured with other materials and geometries than those shown in FIGS. 2 and 3. Dimensions of the various layers may differ, but it is required that the limits of the return electrode-to-patient capacitance be known. The parameters and conditions that affect the capacitance range include: manufacturing variations of geometries, dielectric thickness, variation of dielectric thickness, skin conditions at place of placement, location of placement, and the amount of hair at the site of placement. Of the parameters and conditions that affect the range of capacitance, all can be controlled by manufacturing controls except skin and hair conditions. I have found that proper selection of dielectric thickness and/or material, the effect of skin and hair conditions can be compensated. For example, I found that the range of capacitance of three sample sets of return electrodes, each having a different dielectric thickness varies inversely with the dielectric thickness. The sample set of return electrodes that had the thickest dielectric layer had the narrowest capacitance range. For the preferred embodiment shown in FIGS. 2 and 3, a dielectric thickness of 8 to 20 mil is preferred. A thinner dielectric layer causes the capacitance value to be too sensitive to normal skin conditions, and a thicker dielectric layer reduces sensitivity such that the capacitance value may not be an adequate indication of proper placement.

In another embodiment electrode 32 is divided into several segments and a separate terminal is provided for each of the electrode segments. The return electrode-to-patient capacitance, therefore, is divided into several sections and each section is electronically monitored. The capacitance value of each section could be compared one with the other and/or with an absolute value. This method of comparing capacitance values compensates for some of the skin and placement variables but adds complexity to the safety monitor circuitry.

FIG. 3A shows a partial sectional view of still another embodiment of the return electrode. The embodiment shown in FIG. 3A is generally similar to the embodiment of FIG. 3, and similar numerals are used to designate similar elements.

The return electrode of FIG. 3A requires that the electrosurgery current be capacitively conducted to electrode 30 and terminal 22, and that ohmic contact to the patient be made by an additional terminal such as direct contact with electrode 32. In this embodiment electrode 30 is covered with a dielectric layer 35 which is, for example, a gel impregnated foam or double-sided adhesive. In the embodiment shown, conductive adhesive 37 overlays electrode 32 to provide ohmic contact to the patient and to bond the return electrode to the patient. Alternatively, an optional adhesive 39 around the border of the return electrode is provided, and conductive adhesive 37 is not required since ohmic contact is made by direct contact with the patient's body.

The embodiments shown in FIGS. 2, 3 and 3A are particularly advantageous forms, since they are relatively simple in construction and utilize only a single capacitance. This simplifies the monitoring circuitry of safety monitor 12 of the present invention.

Figure 4A:
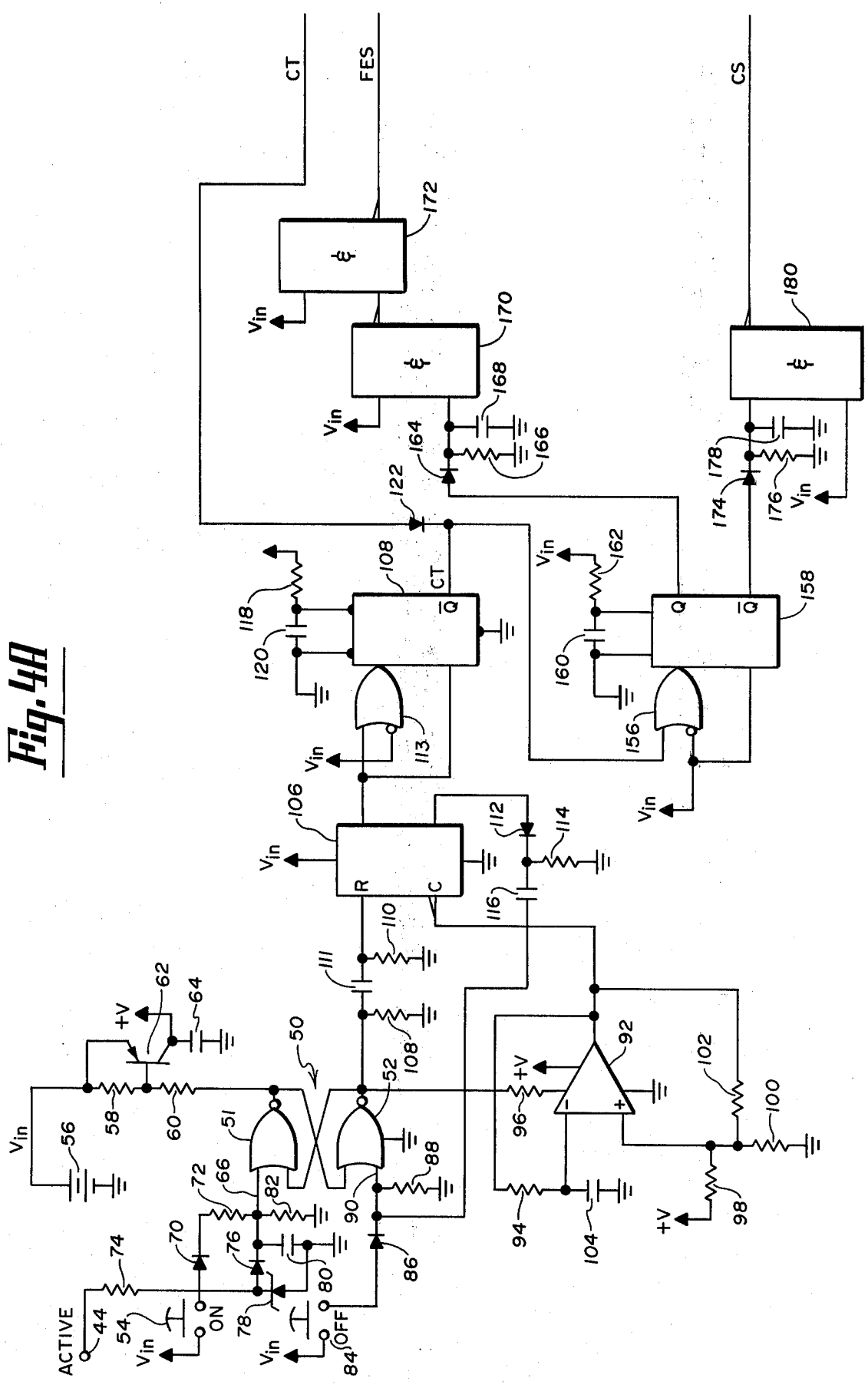
FIGS. 4A and 4B are an electrical schematic diagram of the safety monitor circuit of the present invention.
Figure 4B:
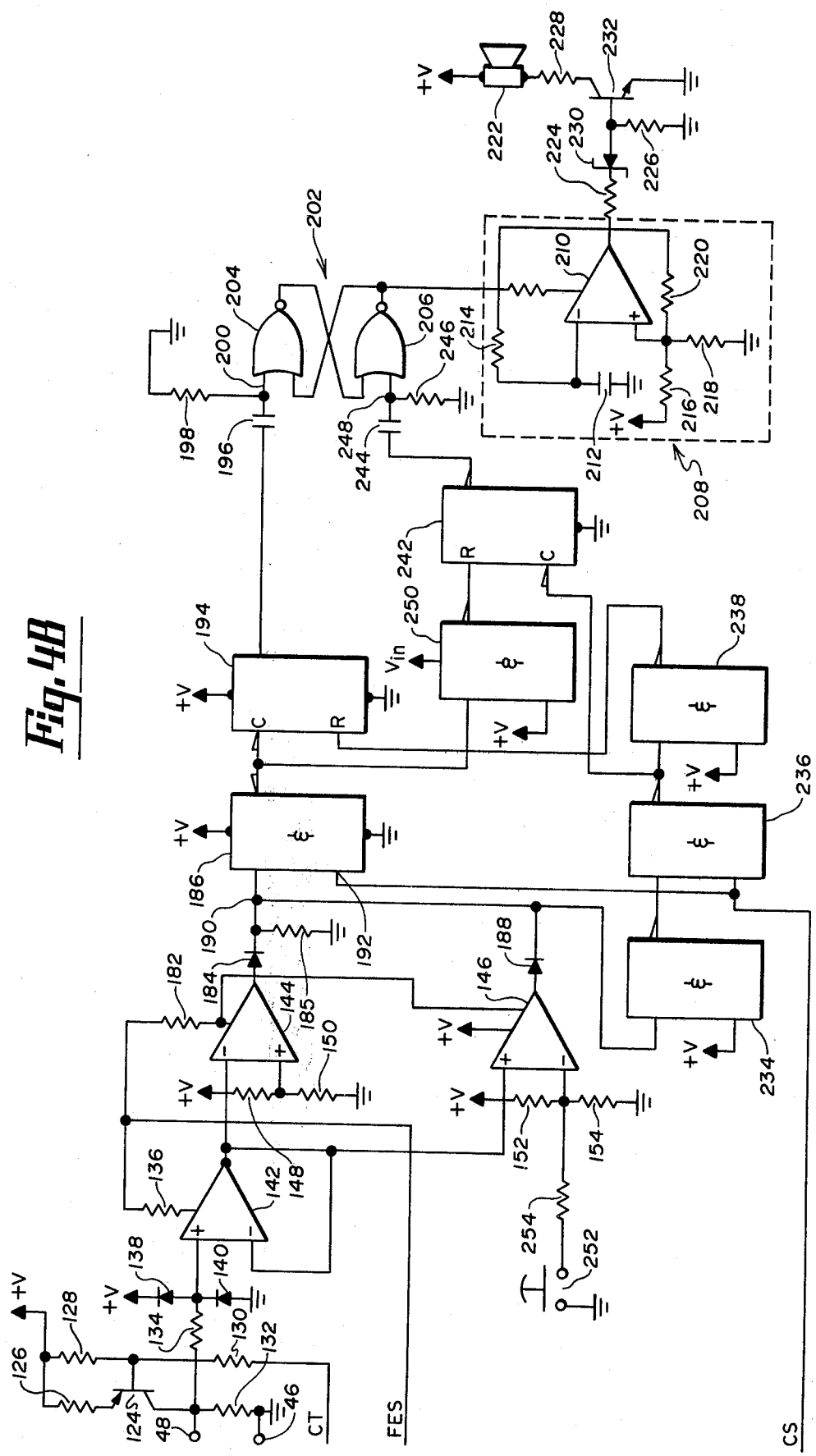

FIGS. 4A and 4B are an electrical schematic diagram of a preferred embodiment of safety monitor 12 of the present invention. The safety monitor includes first terminal 44 (FIG. 4A) for connection to the active line 18, second terminal 46 (FIG. 4B) for connection to return line 20, and third terminal 48 (FIG. 4B) for connection to signal line 24. The portion of the monitor shown in FIG. 4A provides three timing signals designated "CT", "FES", and "CS". The portion of the monitor shown in FIG. 4B measures capacitance between terminals 46 and 48 and provides an alarm signal when the capacitance is outside a predetermined range.

As illustrated in FIG. 4A, the monitor is activated by setting RS flipflop 50, which is formed by NOR gates 51 and 52. This may be accomplished by depressing ON switch 54, or by a voltage pulse at first terminal 44 (produced by a signal on active line 18 of FIG. 1). ON switch 54 has one terminal connected to a supply voltage designated $V_{in}$, which is supplied from a power supply formed by battery 56, resistors 58 and 60, transistor 62, and capacitor 64. The other terminal of ON switch 54 is connected to Set input 66 of flipflop 50 through diode 70 and resistor 72. First terminal 44 is connected to Set input 66 through circuitry including resistor 74, diode 76, Zener diode 78, capacitor 80, and resistor 82.

Also shown in FIG. 4A is OFF switch 84, by which the medical personnel may positively turn off the safety monitor. OFF switch 84 has one terminal connected to the $V_{in}$ power supply, and another terminal connected through input circuitry including diode 86 and resistor 88 to Reset input 90 of flipflop 50.

When flipflop 50 is set either by ON switch 54 being turned on, or by a signal being present at first terminal 44, the output of NOR gate 52 goes high. This high output activates an oscillator formed by amplifier 92, resistors 94, 96, 98, 100 and 102, and capacitor 104. The oscillator output from amplifier 92 is supplied to the Clock input of counter 106. In addition, the output of NOR gate 52 is differentiated and supplied to the Reset input of counter 106 by resistors 108 and 110 and capacitor 111.

One output of counter 106 is supplied to inputs of one-shot 108 both directly, and through OR gate 113. Another (higher order) output of counter 106 is differentiated and fed back to Reset terminal 90 of flipflop 50 by means of diode 112, resistor 114, capacitor 116, and resistor 88.

The $\overline{Q}$ output of one-shot 108 is normally high and is triggered to a low state by the signal supplied from counter 106. Resistor 118 and capacitor 120 determine the time constant of one-shot 108, and therefore the time duration which the $\overline{Q}$ output of one-shot 108 remains low.

The $\overline{Q}$ output of one-shot 108 is designated the CT signal, and controls the charging time of the capacitor formed by return electrode 16 and the patient's body. The CT signal is supplied through diode 122 to a charging circuit (shown in FIG. 4B) which includes transistor 124 and resistors 126, 128, 130 and 132. When transistor 124 is turned on by the CT signal going low, current flows through the emitter-collector current path of transistor 124 to terminal 48 and on signal line 24 to terminal 25 of patient plate 16. This charging current charges of plate-to-patient capacitance. When the CT signal again goes high, transistor 124 turns off and the charging of the capacitance ceases. The voltage between terminals 48 and 46 as a result of this charging is a function of the capacitance between electrodes 30 and 32 of return electrode 16. This capacitance, in turn, is a function of the area of return electrode 16 which is in contact with the patient's body. The voltage appearing between terminals 48 and 46 after charging, therefore, is a function of the area of return electrode 16 in contact with the patient's body.

The remaining circuitry shown in FIG. 4B monitors the voltage between terminals 48 and 46 and provides an alarm signal in the event that the voltage falls outside of the predetermined range. This monitoring of the voltage occurs only at specified times determined by the FES and CS signals provided by the remaining circuitry of FIG. 4A.

The voltage at terminal 48 is buffered by an amplifier circuit including resistors 134 and 136, diodes 138 and 140 and amplifier 142. The output of amplifier 142 is supplied to the inverting input of comparator 144 and the non-inverting input of comparator 146. The output of amplifier 142 is compared by comparator 144 to a first reference voltage established by a voltage divider formed by resistors 148 and 150, which are connected to the non-inverting input of comparator 144. Comparator 146 compares the output of amplifier 142 to a second reference voltage established by a voltage divider formed by resistors 152 and 154. The second reference voltage is applied to the inverting input of comparator 146.

The operation of amplifier 142 and comparators 144 and 146 is controlled by the FES signal. The FES signal is produced when the CT signal goes high after having been low. The CT signal is supplied through OR gate 156 to a one-shot 158. The duration of the FES signal is determined by capacitor 160 and resistor 162 which are connected to one-shot 158. The $\overline{Q}$ output of one-shot 158 is supplied to a circuit including diode 164, resistor 166, capacitor 168, and AND gates 170 and 172. The output of NAND gate 172 is the FES signal.

The CS signal is derived from the $\overline{Q}$ output of one-shot 158 by a circuit including diode 174, resistor 176, capacitor 178 and NAND gate 180.

Figure 5:
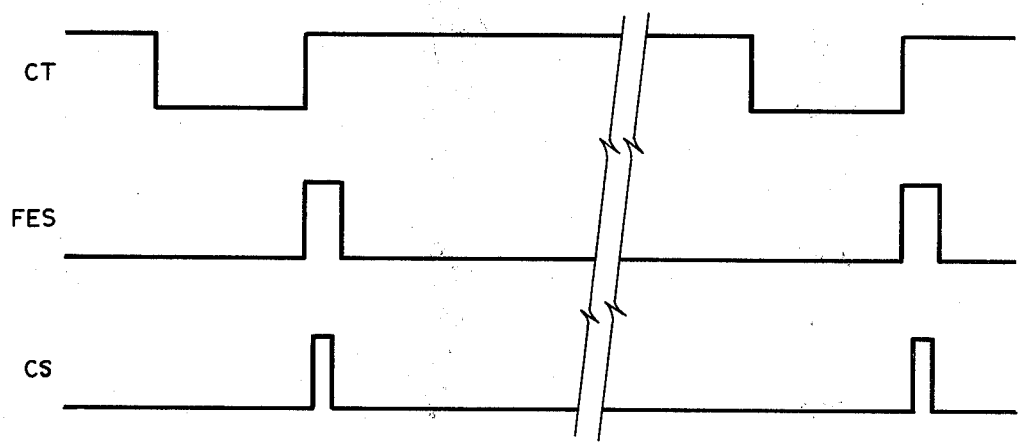
FIG. 5 is a diagram of timing signals generated in the circuit of FIGS. 4A and 4B.

FIG. 5 illustrates the timing of the CT, FES and CS signals. As shown in FIG. 5, both the FES and CS signals are normally low and remain low until the CT signal has switched from low to high, thereby indicating the end of charging of the return electrode-to-patient capacitance. The FES signal then goes high for a duration determined by one-shot 158. The CS signal is delayed slightly in time due to resistor 176 and capacitor 178 and is of shorter duration than the FES signal. As a result, the CS signal pulse occurs within the interval defined by the FES signal pulse.

The FES signal is supplied to the junction of resistors 136 and 182, which in turn are connected to supply power to amplifier 142 and comparators 144 and 146. As long as the FES signal is low, both amplifier 142 and comparators 144 and 146 are disabled. As a result, the voltage between terminals 48 and 46 is not fed through by amplifier 142 and compared by comparators 144 and 146 until the FES signal is supplied. This occurs only after the CT signal has gone high indicating that charging of the return electrode-to-patient capacitance is completed.

If the voltage supplied at the output of amplifier 142 is less than the first reference voltage, the output of comparater 144 goes high. This high signal is supplied by diode 184 and resistor 185 to input 190 of NAND gate 186. Similarly, if the voltage at the output of amplifier 142 is greater than the second reference voltage, the output of comparator 146 goes high. This output is supplied by diode 188 to input 190 of NAND gate 186.

The CS signal is supplied to other input 192 of NAND gate 186. As a result, the status of the output of comparators 144 and 146 (i.e. the signal at input 190) is interrogated each time the CS signal is produced. If an alarm condition exists (i.e. the signal at input 190 is high), the output of NAND gate 186 goes low, thereby providing a pulse to the clock input of alarm pulse counter 194. If no alarm condition exists (i.e. the signal at input 190 is low), the output of NAND gate 186 remains high, and no pulse is supplied to the clock input of counter 194.

The output of alarm pulse counter 194 is connected by capacitor 196 and resistor 198 to Set input 200 of edge triggered RS flipflop 202, which is formed by NOR gates 204 and 206. The output of RS flipflop 202 controls operation of oscillator 208, which is formed by amplifier 210, capacitor 212, and resistors 214, 216, 218 and 220. The output of oscillator 208 is supplied to a circuit for driving sound transducer 222. This circuit includes resistors 224, 226 and 228, Zener diode 230 and transistor 232.

The outputs of comparators 144 and 146 are also supplied to an input terminal of NAND gate 234. If an alarm condition does not exist at the time that the CS signal is produced (i.e. the outputs of both comparators 144 and 146 are low), NAND gates 234, 236 and 238 provide a reset pulse to the Reset input of alarm pulse counter 194.

The output of NAND gate 236 is also supplied to a Clock input of non-alarm pulse counter 242. The output of non-alarm pulse counter 242 is coupled by capacitor 244 and resistor 246 to Reset input 248 of RS flipflop 202.

The output of NAND gate 186, which goes low whenever an alarm condition is present during a CS signal pulse, is also supplied to NAND gate 250. The output of NAND gate 250 is connected to the Reset input of non-alarm pulse counter 242.

The operation of the circuit of FIGS. 4A and 4B is generally as follows. When the monitor is turned on either by depressing switch 54, or by a signal pulse being present at first terminal 44, flipflop 50 is set, which activates the oscillator supplying pulses to counter 106. Each time that counter 106 reaches a first predetermined number of counts, an output pulse is supplied which results in the production of the CT signal. The duration of the CT signal is determined by one-shot 108 and resistor 118 and capacitor 120.

The CT signal turns on transistor 124 (FIG. 4B) which supplies current through second terminal 48 to the capacitance formed by return electrode 16 and the patient's body. When the CT signal again goes high, transistor 124 is turned off, and the charging is completed. This also results in the production of the FES and CS signals.

The FES signals activates buffer 142 and comparators 144 and 146, thereby causing the amplified voltage from the return electrode-to-patient capacitance to be compared to the first and second predetermined voltage levels by comparators 144 and 146, respectively. Provided the amplified voltage level is greater than the first predetermined voltage level and less than the second predetermined voltage level, the outputs of both comparator 144 and comparator 146 remain low indicating a non-alarm condition. When the CS signal is supplied to NAND gate 186, the logic low state at terminal 190 indicates a non-alarm condition during this particular test cycle.

If, on the other hand, the amplified voltage level falls outside of the voltage range defined by the first and second reference voltages, the output of one of the two comparators 144 and 146 goes high. This indicates an alarm condition when the CS signal pulse is received by NAND gate 186. In the event of an alarm condition, the output of NAND gate 186 provides a clock pulse to alarm pulse counter 194, thereby incrementing the alarm pulse count contained in alarm pulse counter 194.

If a predetermined number of capacitance test cycles are performed in which an alarm condition is signalled, the alarm pulse count in counter 194 eventually reaches a value at which the output of counter 194 goes high, thereby setting flipflop 202, turning on oscillator 208, and energizing sound generator 222. Once activated, oscillator 208 continues to operate, and sound generator 222 continues to produce sound until RS flipflop 202 is reset.

The resetting of RS flipflop 202 occurs when the non-alarm pulse count in non-alarm pulse counter 242 reaches a predetermined value. Counter 242 is incremented each time a non-alarm condition occurs when CS signal is supplied. However, if an alarm condition pulse is produced by NAND gate 186, NAND gate 250 resets the count in non-alarm pulse counter 242.

It can be seen, therefore, that in order for sound transducer 222 to be initially activated, a predetermined number of consecutive alarm condition pulses must be supplied to counter 194. Once an alarm condition has been identified and flipflop 202 has been set, it takes a predetermined number of consecutive non-alarm pulses supplied to counter 242 before flipflop 202 is reset and sound transducer 22 is de-activated. For example, in one preferred embodiment the predetermined number of pulses required to produce an output of alarm pulse counter 194 or of non-alarm pulse counter 242 was thirty-two pulses. If in this case twenty-nine alarm condition pulses were received and then a non-alarm condition pulse was received, alarm pulse counter 194 would be reset and a succession of thirty-two consecutive pulses would be required in order to set flipflop 202. Similarly, thirty-two consecutive non-alarm pulses would be required to reset flipflop 202 once an alarm condition has been positively identified and flipflop 202 has been set.

The requirement of a succession of pulses either signalling an alarm or a non-alarm, the strobing of amplifier 142 and comparators 144 and 146, and the clocking of these signals through NAND gate 186 and 236 greatly reduce the chance of a false or nuisance alarm or false non-alarm condition will be identified. This is particularly important since an electrosurgical generator generates an extremely high electrical noise environment.

As an additional aid to reducing nuisance alarm problems, press-to-test switch 252 and resistor 254 are connected to the inverting input of comparator 146. When depressed, switch 252 connects resistor 254 in parallel with resistor 154, thereby reducing the second reference voltage at the inverting input of comparator 146. By the use of switch 252, the attending medical personnel may at the time of placement of return electrode 16 on the patient, and at subsequent times during the surgical procedure, verify that return electrode 16 is making more than just marginal contact with the patient. If return electrode 16 is only making marginal contact with the patient, the medical personnel can rectify the situation before surgery begins.

Another feature of the safety monitor of FIGS. 4A and 4B is that the monitor system is automatically turned on by activation of electrosurgical generator 10, even if the medical personnel forgets to turn the monitor 12 on by means of switch 54. The circuit stays on for a predetermined length of time, and then turns itself off. This occurs when counter 106 finally reaches its count at which the output which is fed back to the reset terminal 90 of flipflop 50 goes high.

The provision of a positive OFF switch 84 permits the medical personnel to temporarily disable the safety monitor. This is particularly advantageous when return electrode 16 is being removed from the patient after surgery has been completed. If the monitor still remains on, removal of return electrode 16 from the patient causes an alarm condition to be sensed and signalled by sound transducer 222. This is an annoying condition which can be immediately terminated by pressing OFF switch 84.

The specific embodiment of the safety monitor shown in FIGS. 4A and 4B continuously monitors return electrode-to-patient capacitance, and thereby the area of contact between the return electrode and the patient's body whenever electrosurgery generator 10 (FIG. 1) is in operation. In another embodiment of the present invention, monitoring of capacitance is performed prior to each time that electrical current is supplied on active line 18 to active electrode 14. In this embodiment, safety monitor 12 receives a signal each time the surgeon wishes to have current applied to active electrode 14. Safety monitor 12 blocks current from flowing on active line 18 to active electrode 14 until the return electrode-to-patient capacitance has been measured and is within the predetermined range. If the return electrode-to-patient capacitance is outside the predetermined range, safety monitor 12 not only provides an alarm signal which activates a sound generator (as in the embodiment shown in FIGS. 4A and 4B), but also causes current to be prevented from reaching active electrode 14. In this embodiment, electrosurgery cannot commence until proper contact has been provided between return electrode 16 and the patient's body such that safety monitor 12 will permit current to be supplied to active electrode 14.

One advantage of this latter embodiment is that safety monitor 12 need not operate during the time when radio frequency current is being supplied to active electrode 14. As a result, noise problems produced by the current supplied to active electrode 14 are eliminated or significantly reduced.

In another embodiment of the present invention, the circuitry of safety monitor 12 is configured to be turned on by a manual ON-OFF switch. The activation of electrosurgical current to active electrode 14 disables sound transducer oscillator 208. With this configuration, the return electrode-to-body capacitance is being monitored all the time. The deactivation of sound transducer oscillator 208 prevents nuisance noise pulses during activation of electrosurgery.

In conclusion, the electrosurgery safety monitor of the present invention has significant advantages over prior art electrosurgery safety devices. First, the safety monitor senses a parameter which is indicative of the area of contact of the return electrode with the patient's body.

Second, the present invention is simple to use, and requires little attention by medical personnel. The monitor circuit can be configured such that even if the medical personnel fails to turn it on, the safety monitor is operative if the electrosurgery generator is operated.

Third, the present invention is useable with a wide variety of return electrode configurations.

Fourth, the present invention is relatively insensitive to skin conditions, thickness of the skin, dryness of the skin, and the presence or absence of hair on the skin.

Fifth, the present invention minimizes the likelihood of false alarm, despite the high electrical noise environment created by the electrosurgery generator.

Sixth, the safety monitor of the present invention also may be operated so as to prevent current from being supplied to the active electrode if an alarm condition exists.

Although the present invention has been described with reference to preferred embodiments, workers skilled in the art will recognize that changes may be made in form and detail without departing from the spirit and scope of the invention.

What is claimed is:

1. In an electrosurgery system having an active electrode and having a return electrode for connection to the body of a patient, the improvement comprising: the return electrode comprising:
    a first surface for contact with the body;
    ohmic contact means exposed at the first surface for providing ohmic contact to the body;
    a first electrically conductive layer isolated electrically from the ohmic contact means;
    a dielectric layer interposed between the conductive layer and the first surface;
    a first electrical terminal connected to the ohmic contact means; and
    a second electrical terminal connected to the first conductive layer;
means connected to the first and second electrical terminals for sensing a capacitance indicative of area of contact between the first surface of the return electrode and the body of the patient; and
means for providing an alarm signal if the area of contact is less than a predetermined amount.

2. The invention of claim 1 wherein the means for providing an alarm signal senses capacitance between the first and second electrical terminals and provides an alarm signal as a function of the sensed capacitance.

3. The invention of claim 2 wherein the means for providing an alarm signal comprises:
    means connected to the first and second electrical terminals for supplying a charging current; and
    means for sensing voltage between the first and second electrical terminals as a result of the charging current.

4. The invention of claim 3 wherein the means for sensing voltage compares the voltage between the first and second electrical terminals with first and second reference voltages and provides a non-alarm pulse signal if the sensed voltage is within a range between the first and second reference voltages, and an alarm pulse signal if the sensed voltage is outside the range.

5. The invention of claim 4 and further comprising:
    means for providing a signal for enabling the means for supplying charging current for a predetermined time period; and
    means for providing a signal for enabling the means for sensing voltage after the predetermined time period.

6. The invention of claims 4 or 5 wherein the means for supplying a charging current and the means for sensing voltage provide a plurality of capacitance test cycles in which charging current is supplied and voltage is sensed.

7. The invention of claim 6 and further comprising:
    alarm pulse counter means for counting the alarm pulse signals; and
    means for providing an alarm signal when the alarm pulse count attains a first predetermined value.

8. The invention of claim 7 and further comprising:
    means for resetting the alarm pulse count after each non-alarm pulse signal.

9. The invention of claim 8 and further comprising:
    non-alarm pulse counter means for counting the non-alarm pulse signals.

10. The invention of claim 8 wherein the means for providing the alarm signal continues to provide the alarm signal until the non-alarm pulse count attains a second predetermined value.

11. The invention of claim 10 and further comprising:
    means for resetting the non-alarm pulse count after each alarm pulse signal.

12. The invention of claim 1 and further comprising:
    adhesive means for adhesively connecting the return electrode to the body.

13. The invention of claim 1 wherein one of the first and second terminals is connected to a return current line of the electrosurgery system.

14. The invention of claim 13 wherein the first terminal is connected to the return current line.

15. The invention of claim 13 wherein the second terminal is connected to the return current line.

16. The invention of claim 1 wherein the ohmic contact means comprises a second electrically conductive layer generally coplanar with and electrically isolated from the first electrically conductive layer.

17. The invention of claim 16 wherein the ohmic contact means further comprises electrically conductive contact means overlying the second electrically conductive layer for contacting the patient's body.

18. The invention of claim 17 wherein the electrically conductive contact means comprises a conductive pad.

19. The invention of claim 18 wherein the conductive pad is a non-conductive pad impregnated with a conductive gel.

20. The invention of claim 17 wherein the electrically conductive contact means comprises a conductive adhesive.

21. The invention of claim 1 wherein the first electrically conductive layer and the dielectric layer substantially surround the ohmic contact means.

22. The invention of claim 1 wherein the ohmic contact means substantially surrounds the first electrically conductive layer and the dielectric layer.

23. The invention of claim 1 and further comprising:
a substrate member;
a first bonding layer bonding the first electrically conductive layer to the substrate member; and
a second bonding layer bonding the dielectric layer to the first electrically conductive layer.

24. The invention of claim 23 and further comprising:
adhesive means overlying the dielectric layer for adhesively connecting the return electrode to the body.

25. The invention of claim 23 or 24 wherein the ohmic contact means comprises:
a second electrically conductive layer attached to the first bonding layer, the second electrically conductive layer being isolated from the first electrically conductive layer and being connected to the first electrical terminal.

26. The invention of claim 1 and further comprising:
means connected to the active electrode for automatically turning on the means for sensing a capacitance and the means for providing an alarm signal when electrical current is provided to the active electrode.

27. The invention of claim 1 and further comprising:
means for preventing electrical current from being provided to the active electrode in response to the alarm signal.

28. The invention of claim 1 wherein the means for providing an alarm signal does not provide the alarm signal when current is supplied to the active electrode.

29. A return electrode for use in an electrosurgery system, the return electrode having a first surface for contact with a patient's body, the return electrode comprising:
ohmic contact means exposed at the first surface for providing ohmic contact to the patient's body;
a first electrically conductive layer isolated electrically from the ohmic contact means;
a dielectric layer overlying the first conductive layer and interposed between the first conductive layer and the first surface;
a first electrical terminal connected to the ohmic contact means; and
a second electrical terminal connected to the first conductive layer; wherein capacitance between the first and second electrical terminals is indicative of the area of contact between the first surface of the return electrode and the body.

30. The invention of claim 31 and further comprising:
adhesive means for adhesively connecting the return electrode to the body.

31. The invention of claim 29 wherein the ohmic contact means comprises a second electrically conductive layer generally coplanar with and electrically isolated from the first electrically conductive layer.

32. The invention of claim 31 wherein the ohmic contact means further comprises electrically conductive contact means overlying the second electrically conductive layer for contacting the patient's body.

33. The invention of claim 32 wherein the electrically conductive contact means comprises a conductive pad.

34. The invention of claim 33 wherein the conductive pad is a non-conductive pad impregnated with a conductive gel.

35. The invention of claim 32 wherein the electrically conductive contact means comprises a conductive adhesive.

36. The invention of claim 29 wherein the first electrically conductive layer and the dielectric layer substantially surround the ohmic contact means.

37. The invention of claim 29 wherein the ohmic contact means substantially surrounds the first electrically conductive layer and the dielectric layer.

38. The invention of claim 29 and further comprising:
a substrate member;
a first bonding layer bonding the first electrically conductive layer to the substrate member; and
a second bonding layer bonding the dielectric layer to the first electrically conductive layer.

39. The invention of claim 38 and further comprising:
adhesive means overlying the dielectric layer for adhesively connecting the return electrode to the body.

40. The invention of claim 38 or 39 wherein the ohmic contact means comprises:
a second electrically conductive layer attached to the first bonding layer, the second electrically conductive layer being isolated from the first electrically conductive layer and being connected to the first electrical terminal.

* * * * *